United States Patent [19]

Carlsson

[11] Patent Number: 4,824,145
[45] Date of Patent: Apr. 25, 1989

[54] COUPLING COMPONENTS

[75] Inventor: Per-Olov A. Carlsson, Sosdala, Sweden

[73] Assignee: Gambro AB, Sweden

[21] Appl. No.: 36,597

[22] Filed: Apr. 10, 1987

[30] Foreign Application Priority Data

Jun. 6, 1986 [SE] Sweden ............................. 8602562

[51] Int. Cl.⁴ ............................................. F16L 21/00
[52] U.S. Cl. ....................................... 285/38; 285/55; 285/331; 285/332; 285/908
[58] Field of Search ................... 285/331, 55, 908, 38, 285/332, 53, 334.3

[56] References Cited

U.S. PATENT DOCUMENTS

| 1,658,525 | 2/1928 | Housley | 285/331 X |
| 2,768,845 | 10/1956 | Samiran | 285/331 |
| 3,338,598 | 8/1967 | Kurtz | 285/55 |
| 3,876,234 | 4/1975 | Harms | 285/38 |
| 4,214,779 | 7/1980 | Losell | 285/93 |
| 4,238,059 | 12/1980 | Caraway et al. | 285/332 X |
| 4,400,019 | 8/1983 | Fruck | 285/331 X |
| 4,484,769 | 11/1984 | Lacey | 285/331 X |
| 4,629,455 | 12/1986 | Kanno | 285/332 X |
| 4,639,019 | 1/1987 | Mittleman | 285/332 |

FOREIGN PATENT DOCUMENTS

| 2510905 | 9/1975 | Fed. Rep. of Germany | 285/908 |
| 2805416 | 9/1978 | Fed. Rep. of Germany | 285/331 |
| 382185 | 10/1932 | United Kingdom | 285/908 |

Primary Examiner—Thomas F. Callaghan
Attorney, Agent, or Firm—Lerner, David, Littenberg, Krumholz & Mentlik

[57] ABSTRACT

Coupling components are disclosed for coupling together tubes and the like including male and female coupling components. The female coupling component described herein includes inner and outer tubular sections, and the inner tubular section includes an orifice having a size adapted to frictionally engage a male coupling component inserted therein. The outer tubular section is adapted to frictionally engage the outer surface of the inner tubular section, and the outer tubular section is substantially rigid, while the inner tubular section is substantially flexible as compared to the outer tubular section, so that axial movement of the outer tubular section when it is being coupled to the male coupling component carries the inner tubular section therewith.

37 Claims, 4 Drawing Sheets

COUPLING COMPONENTS

FIELD OF THE INVENTION

The present invention relates to coupling components. More particularly, the present invention relates to coupling components which include a female part intended to be coupled together with a corresponding coupling component in the form of a male part. Still more particularly, the present invention relates to such coupling components used in the medical field for joining tubes or tubes within other components such as a bag, a dialyzer, an oxygenator, or the like. More particularly, the present invention relates to coupling together devices of this type often referred to as Luer couplings or Luer-Lock couplings which include means for locking together the two components such as cooperating screw threads or parts thereof.

BACKGROUND OF THE INVENTION

In connection with Luer-Lock couplings previously used to lock together two components such as tubes, these Luer-Lock couplings are frequently made of relatively hard material, so that the screw treads used for such locking purposes will hold. By being able to effect this type of locking, it is possible to obtain a relatively good seal between coupling components therewith. In connection with Luer couplings which do not include such a locking mechanism, they are frequently made of a relatively flexible material in the female part, so as to ensure a satisfactory seal.

Because of this, it is often necessary to use different female parts for such Luer couplings with a locking mechanism, and for those without such a locking mechanism. It is most desirable, however, that it be made possible that the same female part can be used in connection with both types of couplings, while at the same time achieving satisfactory sealing and locking therewith.

SUMMARY OF THE INVENTION

In accordance with the present invention, these and other problems have now been solved by the discovery of a coupling component which comprises a female coupling component which is intended to be coupled together with a corresponding male coupling component and which is designed with an inner flexible cylindrical first coupling portion which is provided at its end with an orifice intended to enclose the male portion with a frictional grip, and which is also provided at its other end with means for connection to a tube, bag or the like, and which also includes an outer torsion-proof second coupling portion which is connected to the inner portion in such a manner that the two parts can be made to move together axially. In this manner a supple and effective seal can now be achieved between the male portion and the female portion at the same time as the locking component of the female portion, such a a screw thread or the like, can be formed in the outer coupling portion, which can thus be manufactured from a harder or more rigid material.

In accordance with a preferred embodiment of the present invention, there is provided a female coupling component adapted to be coupled to a male coupling component including a tubular male coupling member, the female coupling component including an inner tubular female coupling member including first and second ends, the first end of the inner female coupling member including a tubular orifice having a size adapted to frictionally engage the tubular male coupling member when inserted therein, the second end of the inner tubular female coupling member including adapter means for connection to a tube member, and an outer tubular female coupling member including an inner passage adapted to frictionally engage the outer surface of the inner tubular female coupling member, the outer tubular female coupling member being substantially rigid and the inner tubular female coupling member being substantially flexible as compared to the outer tubular female coupling member, so that axial movement of the outer tubular female coupling member so as to be coupled to the male coupling component carries the inner tubular female coupling member therewith.

In accordance with one embodiment of the present invention, the female coupling component includes engagement means for engaging the inner tubular female coupling member to the outer tubular female coupling member together so as to maintain them in axial alignment with each other during application of the male coupling component to the female coupling component. In a preferred embodiment, the engagement means comprises aperture means in the outer tubular female coupling member and projection means projecting from the outer surface of the inner tubular female coupling member at a location corresponding to the aperture means whereby the projection means extends through the aperture means. In a most preferred embodiment the aperture means and projection means extend longitudinally along the outer tubular female coupling member and the inner tubular female coupling member, respectively, and most preferably a plurality of aperture means and corresponding projection means are provided.

In accordance with another embodiment of the present invention, the first end of the outer tubular female coupling member includes thread means for engagement with corresponding thread means on the male coupling component so as to permit threadable engagement between the male and female coupling components.

In accordance with another embodiment of the present invention, the first end of the outer tubular female coupling member includes inwardly projecting flange means for engaging the first end of the inner tubular female coupling member so as to axially compress the inner tubular female coupling member upon decoupling of the male coupling component from the female coupling component. In a preferred embodiment the inwardly projecting flange means comprises a hook-shaped flange member facing inwardly from the first end of the outer tubular female coupling member. In a most preferred embodiment, the outer tubular female coupling member also includes clearance means for providing clearance between at least a portion of the first end of the outer tubular female coupling member and the first end of the inner tubular female coupling member so as to facilitate the axial compression of the inner tubular female coupling member upon the decoupling of the male and female coupling components.

In accordance with another embodiment of the present invention, the outer tubular female coupling member includes gripping means on its outer surface to assist in the gripping and rotation of the outer tubular female coupling member.

In accordance with the coupling apparatus of the present invention, there is provided a female coupling component and a male coupling component in which the male coupling component has a first end and a second end, the first end of the male coupling component including a tubular male coupling member extending therefrom and the female coupling component being in the form described above. In a preferred embodiment of the coupling apparatus of the present invention, the male coupling component includes thread means surrounding the tubular male coupling member, and the first end of the outer tubular female coupling member includes thread means for engagement with the thread means on the male coupling component so as to permit threadable engagement between the male and female coupling components.

In accordance with another embodiment of the coupling apparatus of the present invention, the tubular orifice at the first end of the inner tubular female coupling member has a conical configuration including an inner diameter which increases inwardly from the first end thereof, whereby upon insertion of the male coupling component into the female coupling component, axial compression of the inner tubular female coupling component is created.

As discussed above, in order to prevent mutual rotation between the inner and outer tubular female coupling components the outer tubular female coupling component can be provided with one or more holes or slots into which can be engaged projection means from the inner tubular female coupling member. Locking is thus preferably achieved at two or more points at a distance from each other with respect to the longitudinal direction of these members.

As further indicated above, the outer tubular female coupling member is preferably provided with an external thread or a portion of a thread which is intended to cooperate with a corresponding thread on the male component for pulling together the two coupling components. By means of the present invention this external thread can thus be made of a relatively hard material while at the same time the seal between the male and female parts is achieved with the assistance of a more flexible material of the inner tubular female coupling member. Particularly in the medical context, a further advantage of this invention is that the outer tubular female coupling member does not come into contact with the flow passage through the coupling component itself. Consequently, this member can be manufactured from a cheaper material and can be painted or otherwise acted upon without the flow therethrough being affected In accordance with the embodiment discussed above the end of the outer tubular female coupling member includes a hook, flange or the like adapted to compress the inner tubular female coupling member axially upon decoupling, which assists in facilitating decoupling, since such axial compression creates an increase in the inner diameter thereof. This is again further facilitated by use of the clearance created between the inner and outer tubular female coupling members at or near that location.

It is also preferable that the inner tubular female coupling member be fixed to the outer tubular female coupling member in such a way that any pull or traction created in the tube, bag or the like produces a corresponding axial stretching of the inner tubular female coupling member, and in particular at the orifice portion of same which encloses the male coupling member therein. As a result, this will further strengthen the grip on the male portion. Further advantages in terms of tooling and engineering can be obtained if the outer tortion-proof coupling member is joined to the inner flexible cylindrical coupling member in such a way that mutual rotation between them is prevented. In this manner wear on the inner tubular female coupling member will also be reduced.

BRIEF DESCRIPTION OF THE DRAWINGS

The invention can be more fully appreciated with reference to the following detailed description, which in turns refers to the attached drawings in which.

DETAILED DESCRIPTION

Referring to the Figures, in which like reference numerals refer to like portions thereof, FIGS. 1-4 are intended to schematically illustrate the principles behind the present invention. These Figures thus show a female part or component 1 according to this invention, together with a suitable corresponding or matching male part or component 2. The female part 1 consists of an outer torsion-proof part 3 which is composed of a harder or rigid material, and an inner flexible part 4, which is composed of a softer or more flexible material. At the front end of the female part 1, which is intended to face towards the male part 2, there is provided an inner, conical orifice portion 5, which is intended to enclose a corresponding coupling portion 6 on the male part 2 with a frictional grip. At its other end, the inner part 4 is provided with a recess 7 which is intended to serve as a socket for a tube 8. Immediately in front of the orifice portion 5 of the inner part 4 the outer part 3 is provided with a screw thread 9. Furthermore an internal flange 10 is provided inside of this thread, as is shown on a larger scale in FIG. 14, and which cooperates with an external flange 11 located on the inner part 4, which is in turn shown on a larger scale in FIG. 21. In order to alleviate torsion between the outer part 3 and the inner part 4, the latter is provided with two projecting wings 12 and two flanges 13. These components cooperate with holes 14 and slots 15, respectively, in the outer part 3, whose detailed design can best be seen from FIGS. 9-16.

Figure 1:
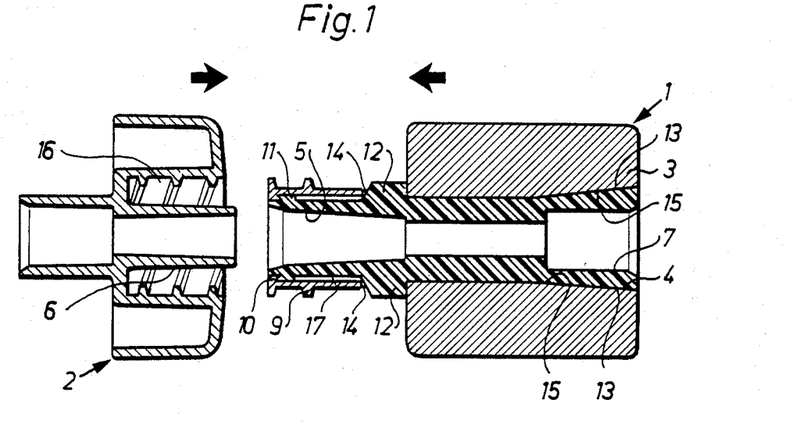
FIG. 1 is a side, elevational, sectional view of male and female coupling components in accordance with the present invention.
Figure 2:
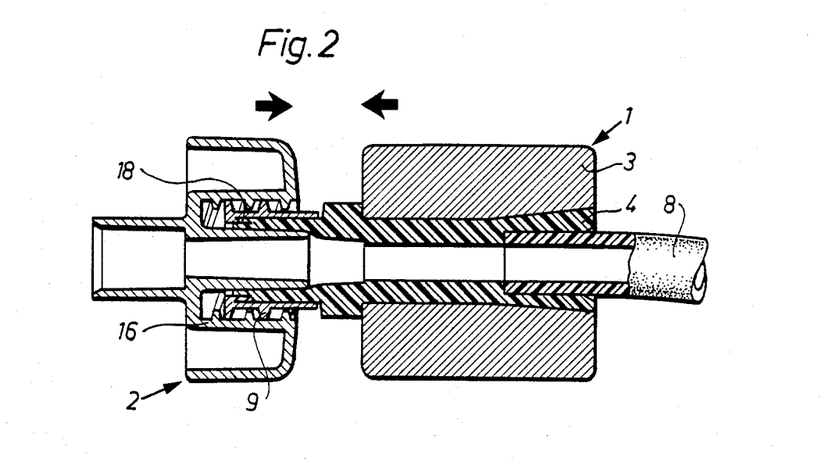
FIG. 2 is a side, elevational, sectional view of the male and female coupling components of FIG. 1 during coupling together thereof.
Figure 3:
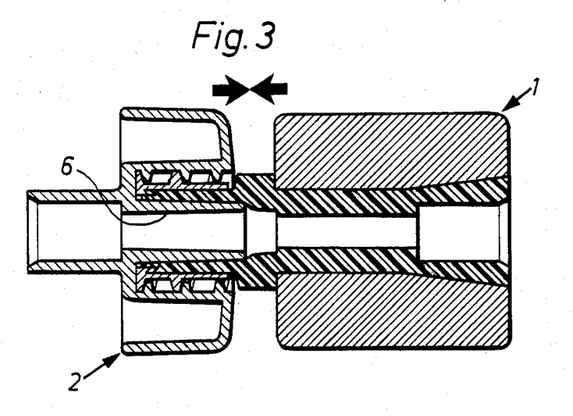
FIG. 3 is a side, elevational, sectional view of the male and female coupling components of FIG. 1 coupled together.

The coupling together of the female part 1 with the male part 2 is illustrated in FIG. 2. The two parts are thus pulled together with the assistance of the screw thread 9 on the female part, and the screw thread 16 on the male part. In doing so, the inner part 4 becomes axially compressed, so that the clearance 17 shown in FIG. 1 wholly or partly disappears. At the same time, a smaller clearance 18 is created between the hook-like flanges 10 and 11. Because of this compression, the orifice portion 5 is slightly expanded, thereby facilitating coupling together of the male and female coupling components. In FIG. 3 the two coupling components are shown fully joined together. Because of the frictional forces, the greater portion of the axial compression which has been created persists. If it slackens slightly, however, the frictional grip around the component 6 on the male part 2 will instead increase.

Figure 4:
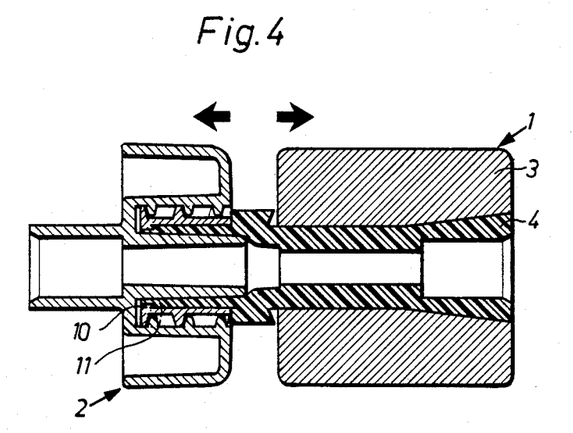
FIG. 4 is a side, elevational, sectional view of the male and female coupling components of FIG. 3 during decoupling thereof.
Figure 5:
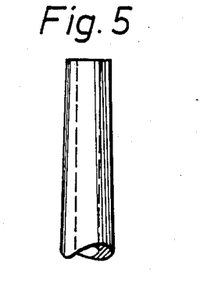
FIG. 5 is a partial, elevational view of a portion of a male coupling component in accordance with the present invention.
Figure 6:
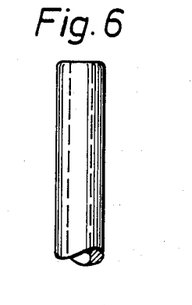
FIG. 6 is a partial, elevational view of a portion of another male coupling component in accordance with the present invention.
Figure 7:
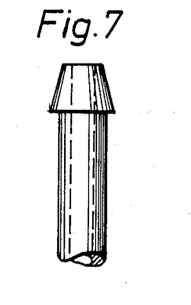
FIG. 7 is a partial, elevational view of a portion of another male coupling component in accordance with the present invention.
Figure 8:
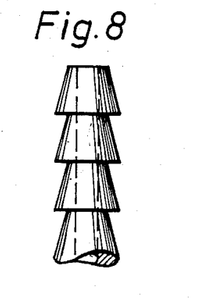
FIG. 8 is a partial, elevational view of a portion of another male coupling component in accordance with the present invention.

Decoupling is illustrated in FIG. 4. When the outer part 3 is twisted in order to effect such decoupling, the hook-like components 10 and 11 engage one another, and axial compression of the inner part 4 is achieved, which thus causes the inner diameter of the orifice portion 5 to increase slightly, so that separation of the components is facilitated thereby.

By the use of these components, traction occurs in the tube 8, an axial stretching of the inner part 4 is produced thereby, especially in Luer couplings which do not include screw thread locking. This, in turn, creates an increase in the frictional grip between component 6 and the orifice portion 5 enclosing same.

A preferred embodiment of the outer part of a female coupling component in accordance with the invention is shown in FIGS. 9-16. Similarly, a preferred embodiment of the inner part of the same female coupling component is shown in FIGS. 17-22. Since this embodiment substantially corresponds to that shown in FIGS. 1-4, the same reference numerals have been used therein. In FIGS. 9-22, however, the two parts are shown in greater detail.

Figure 9:
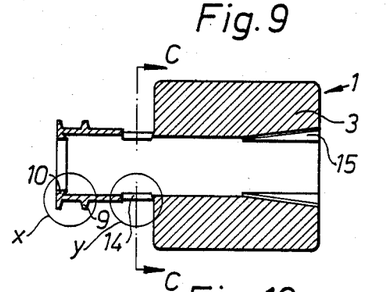
FIG. 9 is a side, elevational, sectional view of the outer tubular female coupling member in accordance with the present invention, taken along lines A—A of FIG. 10.
Figure 14:
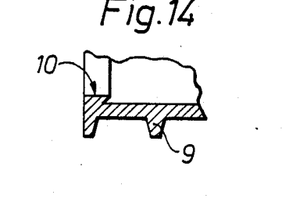
FIG. 14 is a partial, elevational, sectional view of the portion of the outer tubular female coupling member shown in circle x in FIG. 9.
Figure 15:
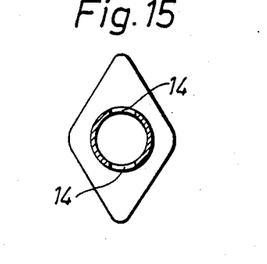
FIG. 15 is an elevational, partially sectional view of the outer tubular female coupling member of FIG. 9, taken along line C—C thereof.
Figure 16:
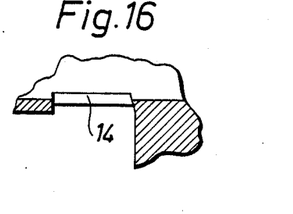
FIG. 16 is a partial, elevational, sectional view of the portion of the outer tubular female coupling member of FIG. 9 shown in circle y thereof.

As is evident from FIG. 9, slots 15 are angled. This facilitates insertion of the inner part 4 with its projecting wings 12. After such insertion, flanges 13, shown for example in FIG. 18, completely fill slots 15. The screw thread 9 and the hole 14, respectively, inside the circles marked x and y in FIG. 9, are shown on a larger scale in FIGS. 14 and 16, respectively. In FIG. 14 the hook-like flange 10 is also evident.

Figures 10, 13:
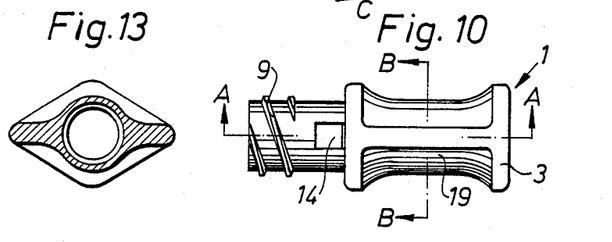
FIG. 10 is a side, elevational view of the outer tubular female coupling member of FIG. 9.
FIG. 13 is an elevational, partially sectional view of the outer tubular female coupling member of FIG. 10, taken along line B—B thereof.
Figure 11:
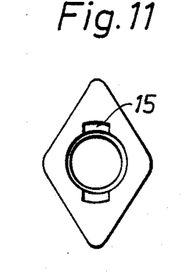
FIG. 11 is an end, elevational view of the outer tubular female coupling member of FIG. 9, taken from the right side.
Figure 12:
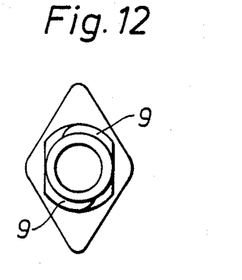
FIG. 12 is an end, elevational view of the outer tubular female coupling member of FIG. 9, taken from the left side thereof.

In FIG. 10, it is shown how the outer part 3 has been designated with appropriately shaped gripping surfaces 19, which are suitable for compression, traction, and torsion.

Figure 17:
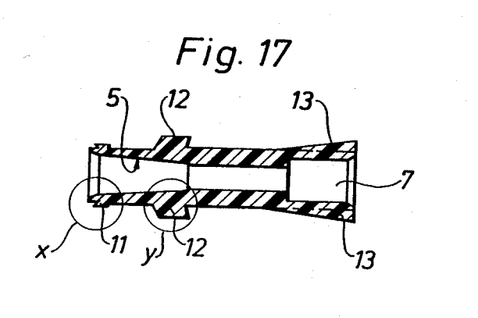
FIG. 17 is a side, elevational, sectional view of an inner tubular female coupling member in accordance with the present invention, taken along line A—A of FIG. 18.
Figure 18:
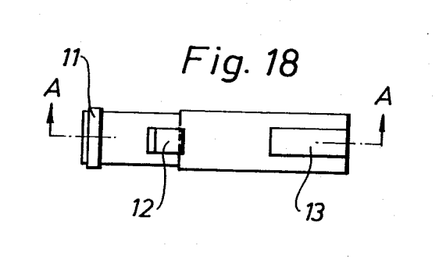
FIG. 18 is a side, elevational view of the inner tubular female coupling member of FIG. 17.
Figure 19:
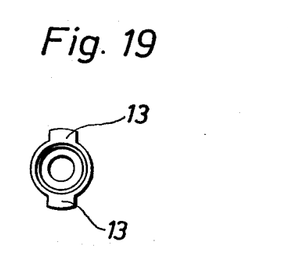
FIG. 19 is a side, elevational view of the inner tubular female coupling member of claim 17 taken from the right side thereof.
Figure 20:
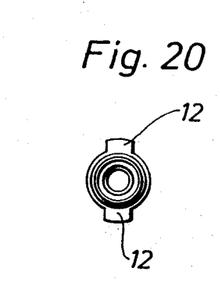
FIG. 20 is a side, elevational view of the inner tubular female coupling member of FIG. 17 taken from the left side thereof.
Figure 21:
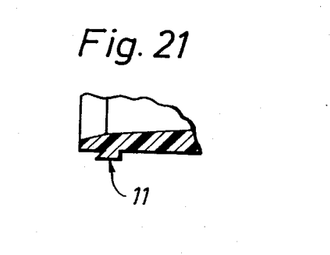
FIG. 21 is a side, elevational, sectional view of the portion of the inner tubular female coupling member of FIG. 17 shown in circle x thereof.
Figure 22:
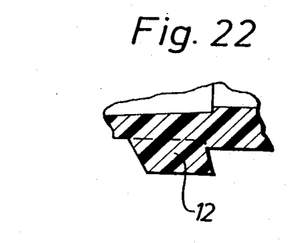
FIG. 22 is a side, elevational, sectional view of the portion of the inner tubular female coupling member of FIG. 17 shown in circle y thereof.

Those components marked as x and y in FIG. 17 are shown on a larger scale in FIGS. 21 and 22, respectively. In this case, the hooked flange 11 and one of the wings 12 are also evident. These components are also shown more clearly in FIG. 18. The design of the flanges 13 is best shown by a comparison of FIGS. 17 and 18. Since the components according to FIGS. 9-22 function in substantially the same manner as those shown in FIGS. 1-4, no further description of same is required.

FIGS. 5-8 show examples of four different male coupling members which may be used advantageously with the female part according to this invention, including that case without any special screw thread for locking purposes. Upon coupling together these components, the soft inner part 4 behaves essentially in the same manner as is the case upon coupling with component 6 as shown in FIGS. 1-4. The same applies to decoupling.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. A female coupling component adapted to be alternately coupled to and released from a male coupling component including a tubular male coupling member, said female coupling component comprising an inner tubular female coupling member including a first end and a second end, said first end of said inner tubular female coupling member including a tubular orifice having a size adapted to frictionally engage said tubular male coupling member when inserted therein, said second end of said inner tubular female coupling member including adapter means for connection to a tube member, and an outer tubular female coupling member including an inner passage adapted to engage the outer surface of said inner tubular female coupling member, said outer tubular female coupling member being substantially rigid and said inner female coupling member being substantially resilient as compared to said outer tubular female coupling member and being axially compressible, whereby axial movement of said outer tubular female coupling member so as to be coupled to said male coupling component carries said inner tubular female coupling member therewith, and said inner tubular female coupling member may be axially compressed thereby.

2. The female coupling component of claim 1 including structural engagement means for structurally engaging said inner tubular female coupling member to said outer tubular female coupling member together so as to maintain said inner and outer female coupling members in axial alignment with each other during application of said male coupling component to said female coupling component.

3. The female coupling component of claim 2 wherein said structural engagement means comprises aperture means in said outer tubular female coupling member and projection means integral with and projecting from said outer surface of said inner tubular female coupling member at a location corresponding to said aperture means whereby said projection means extends through said aperture means.

4. The female coupling component of claim 3 wherein said aperture means and said projection means extend longitudinally along said outer tubular female coupling member and said inner tubular female coupling member, respectively.

5. The female coupling component of claim 4 including a plurality of said aperture means and said corresponding projection means.

6. The female coupling component of claim 1 wherein said first end of said outer tubular female coupling member includes thread means for engagement with corresponding thread means on said male coupling component so as to permit threadable engagement between said male coupling component and said female coupling component.

7. The female coupling component of claim 1 wherein said outer tubular female coupling member includes gripping means on the outer surface thereof, so as to assist in the gripping and rotation of said outer tubular female coupling member.

8. The female coupling component of claim 1 wherein said inner tubular female coupling member is at least partly expandable within the outer tubular female coupling member.

9. A female coupling component adapted to be alternately coupled to and released from a male coupling component including a tubular male coupling member, said female coupling component comprising an inner tubular female coupling member including a first end and a second end, said first end of said inner tubular female coupling member including a tubular orifice having a size adapted to frictionally engage said tubular male coupling member when inserted therein, said second end of said inner tubular female coupling member including adapter means for connection to a tube member, and an outer tubular female coupling member including an inner passage adapted to engage the outer surface of said inner tubular female coupling member, said outer tubular female coupling member being substantially rigid and said inner female coupling member being substantially resilient as compared to said outer tubular female coupling member and being axially compressible, whereby axial movement of said outer tubular female coupling member so as to be coupled to said male coupling component carries said inner tubular female coupling member therewith, and said inner tubular female coupling member may be axially compressed thereby, and wherein said first end of said outer tubular female coupling member includes inwardly projecting flange means for engaging said first end of said inner tubular female coupling member so as to axially compress said inner tubular female coupling member upon the decoupling of said male coupling component from said female coupling component.

10. The female coupling component of claim 9 wherein said inwardly projecting flange means comprises a hook-shaped flange member facing inwardly from said first end of said outer tubular female coupling member.

11. The female coupling component of claim 10 wherein said outer tubular female coupling member includes clearance means for providing a clearance between at least a portion of said first end of said outer tubular female coupling member and said first end of said inner tubular female coupling member so as to facilitate said axial compression of said inner tubular female coupling member upon said decoupling of said male coupling component from said female coupling component.

12. Coupling apparatus comprising a female coupling component and a male coupling component for alternately coupling thereto and releasing therefrom, said male coupling component having a first end and a second end, said first end of said male coupling component including a tubular male coupling member extending therefrom, said female coupling component comprising an inner tubular female coupling member including a first end and a second end, said first end of said inner tubular female coupling member including a tubular orifice having a size adapted to frictionally engage said tubular male coupling member upon coupling of said male coupling component to said female coupling component, said second end of said inner tubular female coupling member including adapter means for connection to a tube member, and an outer tubular female coupling member including an inner passage adapted to engage the outer surface of said inner tubular female coupling member, said outer tubular female coupling member being substantially rigid and said inner tubular female coupling member being substantially resilient as compared to said outer tubular female coupling member and being axially compressible, whereby axial movement of said outer tubular female coupling member so as to be coupled to said male coupling component carries said inner tubular female coupling member therewith, and said inner tubular female coupling member may be axially compressed thereby.

13. The coupling apparatus of claim 12 wherein said female coupling component includes structural engagement means for structurally engaging said inner tubular female coupling member to said outer tubular female coupling member together so as to maintain said inner and outer tubular female coupling members in axial alignment with each other during application of said male coupling component to said female coupling component.

14. The coupling apparatus of claim 13 wherein said structural engagement means comprises aperture means in said outer tubular female coupling member and projection means integral with and projecting from said outer surface of said inner tubular coupling member at locations corresponding to said aperture means, whereby said projection means extends through said aperture means.

15. The coupling apparatus of claim 14 wherein said aperture means and said projection means extend longitudinally along said outer tubular female coupling member and said inner tubular female coupling member, respectively.

16. The coupling apparatus of claim 13 including a plurality of said aperture means and said corresponding projection means.

17. The coupling apparatus of claim 12 wherein said male coupling component includes thread means surrounding said tubular male coupling member, and wherein said first end of said outer tubular female coupling member includes thread means for engagement with said thread means of said male coupling component so as to permit threadable engagement between said male coupling component and said female coupling component.

18. The coupling apparatus of claim 12 wherein said tubular orifice at said first end of said inner tubular female coupling member has a conical configuration including an inner diameter which decreases inwardly from said first end thereof, whereby upon insertion of said male coupling component into said female coupling component an axial compression of said inner tubular female coupling component is created.

19. The coupling apparatus of claim 12 wherein said outer tubular female coupling member includes gripping means on the outer surface thereof, so as to assist in gripping and rotation of said outer tubular female coupling member.

20. The coupling apparatus of claim 12 wherein said inner tubular female coupling member is at least partly expandable within the outer tubular female coupling member.

21. Coupling apparatus comprising a female coupling component and a male coupling component for alternately coupling thereto and releasing therefrom, said male coupling component having a first end and a second end, said first end of said male coupling component including a tubular male coupling member extending therefrom, said female coupling component comprising an inner tubular female coupling member including a first end and a second end, said first end of said inner tubular female coupling member including a tubular orifice having a size adapted to frictionally engage said tubular male coupling member upon coupling of said male coupling component to said female coupling component, said second end of said inner tubular female coupling member including adapter means for connection to a tube member, and an outer tubular female coupling member including an inner passage adapted to engage the outer surface of said inner tubular female coupling member, said outer tubular female coupling member being substantially rigid and said inner tubular female coupling member being substantially resilient as compared to said outer tubular female coupling member and being axially compressible, whereby axial movement of said outer tubular female coupling member so as to be coupled to said male coupling component carries said inner tubular female coupling member therewith, and said inner tubular female coupling member may be axially compressed thereby, and wherein said first end of said outer tubular female coupling member includes inwardly projecting flange means for engaging said first end of said inner tubular female coupling member so as to axially compress said inner tubular female coupling member upon the decoupling of said male coupling component from said female coupling component.

22. The coupling apparatus of claim 21 wherein said inwardly projecting flange means comprises a hook-shaped flange member facing inwardly from said first end of said outer tubular female coupling member.

23. The coupling apparatus of claim 22 wherein said outer tubular coupling member includes clearance means for providing a clearance between at least a portion of said first end of said outer tubular female coupling member and said first end of said inner tubular female coupling member so as to facilitate said axial compression of said inner tubular female coupling member upon said decoupling of said male coupling component from said female coupling component.

24. Coupling apparatus comprising a female coupling component and a male coupling component for alternately coupling thereto and releasing therefrom, said male coupling component having a first end and a second end, said first end of said male coupling component including a tubular male coupling member extending therefrom, said female coupling component comprising an inner tubular female coupling member including a first end and a second end, said first end of said inner tubular female coupling member including a tubular orifice having a size adapted to frictionally engage said tubular male coupling member upon coupling of said male coupling component to said female coupling component, said second end of said inner tubular female coupling member including adapter means for connection to a tube member, and an outer tubular female coupling member including an inner passage adapted to engage the outer surface of said inner tubular female coupling member, said outer tubular female coupling member being substantially rigid and said inner tubular female coupling member being substantially resilient as compared to said outer tubular femal coupling member and being axially compressible, whereby axial movement of said outer tubular female coupling member so as to be coupled to said male coupling component carries said inner tubular female coupling member therewith, and wherein said male coupling component further includes female coupling means annularly surrounding said tubular male coupling member, and wherein said first end of said outer tubular female coupling member includes male coupling means for cooperative engagement with said female coupling means of said male coupling component, whereby said inner tubular female coupling member will be axially compressed when said female coupling means of said male coupling component receives said male coupling means of said female coupling member, and wherein said first end of said outer tubular female coupling member includes second axial compressing means for further axial compression of said inner tubular female coupling member.

25. The coupling apparatus of claim 24, wherein said female coupling means includes internally projecting screw threads and said male coupling means includes externally projecting screw threads for threadedly engaging said internally projecting screw threads of said female coupling means.

26. The coupling apparatus of claims 24 or 25 wherein said second axial compressing means includes inwardly projecting flange means for engaging said first end of said inner tubular female coupling member so as to axially compress said inner tubular female coupling member upon decoupling of said male coupling component from said female coupling component.

27. The coupling apparatus of claim 26 wherein said inwardly projecting flange means comprises a hook-shaped flange member facing inwardly in the lingitudinal direction from said first end of said outer tubular female coupling member.

28. The coupling apparatus of claim 26 wherein said inwardly projecting flange means engages a outwardly projecting flange disposed at said first end of said inner tubular female coupling member.

29. The coupling apparatus of claim 28 wherein said inwardly projecting flange means and said outwardly projecting flange are hook-shaped for cooperative engagement with each other.

30. A female coupling component adapted to be releasably coupled to a male coupling componenet including a tubular male coupling member, said female coupling component comprising an inner tubular female coupling member having a first end and second end, said first end of said inner tubular female coupling member including a tubular orifice having an internal wall adapted to frictionally engage said tubular male coupling member upon insertion thereinto, said second end of said inner tubular female coupling member including adapter means for connection to a tube member, and an outer tubular female coupling member including an inner passage having an interior surface adapted to engage the outer surface of said inner tubular female coupling member, said outer tubular female coupling member geing substantially rigid, said inner tubular female coupling member geing substantially resilient as compared to said outer tubular female coupling member, whereby axial movement of said outer tubular female coupling member so as to be coupled to said male coupling component carries said inner tubular female coupling member therewith, said outer tubular female coupling member further including inwardly projecting flange means for engaging said first end of said inner tubular female coupling member so as to axially compress said inner tubular female coupling member upon the decoupling of said male coupling component from said female coupling component and clearance means for providing a clearance between at least a portion of said first end of said outer tubular female coupling member and said first end of said inner tubular female coupling member so as to facilitate said axial compression of said inner tubular female coupling member upon said decoupling of said male coupling component from said female coupling component.

31. The female coupling component of claim 30 wherein said inwardly projecting flange means comprises a hook-shaped flange member facing inwardly in the longitudinal direction from said first end of said outer tubular female coupling member.

32. The female coupling component of claim 30 including engagement means for engaging said inner tubular female coupling member to said outer tubular female coupling member together so as to maintain said inner and outer female coupling members in axial alignment with each other during application of said male coupling component to said female component.

33. The female coupling component of claim 32 wherein said engagement means comprises aperture means in said outer tubular female coupling member and projection means projecting from said outer surface of said inner tubular female coupling member at a location corresponding to said aperture means whereby said projection means extends through said aperture means.

34. The female coupling component of claim 33 wherein said aperture means and said projection means extend longitudinally along said outer tubular female coupling member and said inner tubular female coupling member, respectively.

35. The female coupling component of claim 34 including a plurality of said aperture means and said corresponding projection means.

36. The female coupling component of claim 30 wherein said first end of said outer tubular female coupling member includes thread means for engagement with corresponding thread means on said male coupling compnent so as to permit threadable engagement between said male coupling component and said female coupling component.

37. The female coupling component of claim 30 wherein said outer tubular female coupling member includes gripping means on the outer surface thereof, so as to assist in the gripping and rotation of said outer tubular female coupling member.

* * * * *

UNITED STATES PATENT AND TRADEMARK OFFICE
CERTIFICATE OF CORRECTION

PATENT NO. : 4,824,145

DATED : April 25, 1989

INVENTOR(S) : Carlsson, Per-Olov A.

It is certified that error appears in the above-identified patent and that said Letters Patent is hereby corrected as shown below:

Column 9, line 11 "claim 13" should read -- claim 15 --.

Column 10, line 41, "femal" should read -- female --.

Column 11, lines 8-9, "lingitudinal" should read -- longitudinal --.

Column 11, lines 34 & 35, "geing" should read -- being --.

Column 12, line 39, "compnent" should read -- component --.

Signed and Sealed this

Fifth Day of December, 1989

*Attest:*

JEFFREY M. SAMUELS

*Attesting Officer*     Acting Commissioner of Patents and Trademarks